(12) United States Patent
Carpenter

(10) Patent No.: US 11,065,401 B2
(45) Date of Patent: Jul. 20, 2021

(54) STAND FOR MEDICAMENT DELIVERY DEVICE, AND SYSTEM COMPRISING STAND AND MEDICAMENT DELIVERY DEVICE

(71) Applicant: SHL MEDICAL AG, Zug (CH)

(72) Inventor: Lucas Carpenter, New Taipei (TW)

(73) Assignee: SHL MEDICAL AG, Zug (CH)

(*) Notice: Subject to any disclaimer, the term of this patent is extended or adjusted under 35 U.S.C. 154(b) by 0 days.

(21) Appl. No.: 16/688,626

(22) Filed: Nov. 19, 2019

(65) Prior Publication Data
US 2020/0155774 A1 May 21, 2020

(30) Foreign Application Priority Data
Nov. 21, 2018 (EP) ..................................... 18207446

(51) Int. Cl.
*A61M 15/00* (2006.01)
*F16B 47/00* (2006.01)
(Continued)

(52) U.S. Cl.
CPC ......... *A61M 15/0001* (2014.02); *F16B 47/00* (2013.01); *F16M 11/04* (2013.01); *F16M 13/022* (2013.01); *A61M 2209/084* (2013.01); *B01L 9/00* (2013.01); *B01L 9/06* (2013.01); *B01L 2200/023* (2013.01);
(Continued)

(58) Field of Classification Search
CPC .............. B65D 23/001; B65D 2313/06; B65D 21/086; A47G 23/0225; A47G 23/0216; A47G 23/0208; A61J 1/16; B01L 2300/123; B01L 2200/023; B01L 9/06; B01L 9/00; A61M 15/0001; A61M 2209/084;
(Continued)

(56) References Cited

U.S. PATENT DOCUMENTS 1,753,611 A * 4/1930 Lower .................. B43M 99/008
215/12.1
1,865,957 A * 7/1932 Priest ..................... A61C 13/24
433/186
(Continued)

FOREIGN PATENT DOCUMENTS

EP 0414644 A2 2/1991
EP 2799884 A1 11/2014

*Primary Examiner* — Jonathan Liu
*Assistant Examiner* — Taylor L Morris
(74) *Attorney, Agent, or Firm* — McDonnell Boehnen Hulbert & Berghoff LLP

(57) ABSTRACT

A stand for an elongated medicament delivery device having a distal end and a proximal end the stand comprising a base section for supporting the stand on a support surface; a holding section for receiving the distal end of the medicament delivery device; and a body section arranged between the base section and the holding section; wherein the holding section is configured to hold the medicament delivery device in a substantially vertical orientation when the base section is positioned on the support surface. The holding section comprises an elastically deformable material for providing an elastic squeeze fit around the distal end of the medicament delivery device when received in the holding section. A system comprising an elongated medicament delivery device and a stand for supporting the medicament delivery device is also provided.

15 Claims, 3 Drawing Sheets

(51) Int. Cl.
*F16M 11/04* (2006.01)
*F16M 13/02* (2006.01)
*B65D 21/08* (2006.01)
*B01L 9/06* (2006.01)
*B01L 9/00* (2006.01)
*B65D 23/00* (2006.01)
*A61M 5/00* (2006.01)

(52) U.S. Cl.
CPC ....... *B01L 2300/123* (2013.01); *B65D 21/086* (2013.01); *B65D 23/001* (2013.01); *F16M 2200/08* (2013.01)

(58) Field of Classification Search
CPC ..... A61M 5/008; F16M 11/04; F16M 13/022; F16M 2200/08; F16B 47/00
See application file for complete search history.

(56) References Cited

U.S. PATENT DOCUMENTS

| | | | | |
|---|---|---|---|---|
| 1,892,140 | A * | 12/1932 | Fogler | B65D 51/249 222/105 |
| 2,278,075 | A * | 3/1942 | Hecht | A47K 10/14 248/205.5 |
| 2,319,727 | A * | 5/1943 | Duggan | F16B 47/00 248/205.9 |
| 2,908,473 | A * | 10/1959 | Snyder | A47G 23/0241 248/683 |
| 2,940,713 | A * | 6/1960 | Van Dusen | F16B 47/00 248/205.8 |
| 2,963,256 | A * | 12/1960 | Borah | A47G 23/0225 248/346.04 |
| 2,968,888 | A * | 1/1961 | Borah | A47K 1/08 248/346.11 |
| 3,807,713 | A * | 4/1974 | Cornett, III | B65D 1/04 261/122.1 |
| 4,101,044 | A * | 7/1978 | Paquette | B65D 51/249 215/228 |
| 4,552,275 | A * | 11/1985 | Chang | B65D 23/001 215/372 |
| 4,726,553 | A * | 2/1988 | Wischusen, III | A47G 23/0216 215/393 |
| 4,756,497 | A * | 7/1988 | Lan | A47G 23/03 220/630 |
| 4,955,493 | A * | 9/1990 | Touzani | B65D 1/0292 215/372 |
| 5,201,893 | A * | 4/1993 | Holloway | A61M 3/0295 206/571 |
| 5,575,398 | A * | 11/1996 | Robbins, III | A47G 23/0241 220/8 |
| 5,850,917 | A | 12/1998 | Denton et al. | |
| 5,860,559 | A * | 1/1999 | Wang | A47G 23/0208 220/737 |
| 5,961,086 | A | 10/1999 | Moore et al. | |
| 6,497,394 | B1 * | 12/2002 | Dunchock | A47G 23/0225 248/205.8 |
| 6,596,374 | B1 * | 7/2003 | Adjeleian | B60N 3/103 206/490 |
| 7,178,766 | B2 * | 2/2007 | Forshee | B01F 15/00733 248/146 |
| 7,216,837 | B2 * | 5/2007 | Pineda | A47G 7/025 248/104 |
| 7,415,996 | B2 * | 8/2008 | Favreau | A47G 23/0241 141/364 |
| 7,654,402 | B2 * | 2/2010 | Kusuma | B65D 21/086 220/8 |
| 7,712,625 | B2 * | 5/2010 | Alger | A47G 23/0313 220/737 |
| 7,726,621 | B1 * | 6/2010 | Dellinger | B44D 3/14 248/346.5 |
| 8,186,642 | B2 * | 5/2012 | Weiss-Vons | B65H 75/143 248/683 |
| 8,998,158 | B2 * | 4/2015 | St. Jacques | A47J 36/34 248/346.5 |
| 9,044,082 | B2 * | 6/2015 | Kusuma | A45F 3/20 |
| 9,399,297 | B2 * | 7/2016 | Cho | F16B 47/00 |
| 9,968,469 | B2 * | 5/2018 | Muller | A61F 2/7812 |
| 2005/0205752 | A1 * | 9/2005 | Pauli | B65D 23/001 248/680 |
| 2006/0222573 | A1 | 10/2006 | Itoh | |
| 2008/0011925 | A1 * | 1/2008 | Ruff | B60N 3/103 248/310 |
| 2008/0265108 | A1 * | 10/2008 | Felici | A47J 36/34 248/127 |
| 2011/0094991 | A1 * | 4/2011 | Klein | B65D 51/249 215/395 |
| 2011/0114656 | A1 * | 5/2011 | Tupy | A47G 23/0225 220/729 |
| 2011/0311688 | A1 * | 12/2011 | Becraft | B65D 77/003 426/111 |
| 2012/0112030 | A1 * | 5/2012 | Jones | A47B 91/028 248/346.11 |
| 2013/0001392 | A1 * | 1/2013 | Lin | F16B 47/00 248/346.03 |
| 2016/0207678 | A1 * | 7/2016 | Tuan | A47B 97/00 |
| 2017/0027358 | A1 * | 2/2017 | Weissbart | A47G 23/03 |
| 2017/0231869 | A1 * | 8/2017 | Zerebny | A61J 1/16 248/206.2 |
| 2018/0213979 | A1 * | 8/2018 | Dumler | B01F 15/00772 |
| 2018/0296013 | A1 * | 10/2018 | Frei | B65D 23/001 |
| 2019/0046744 | A1 * | 2/2019 | French | A61M 11/042 |
| 2019/0247278 | A1 * | 8/2019 | Gitman | A61M 5/3213 |

* cited by examiner

STAND FOR MEDICAMENT DELIVERY DEVICE, AND SYSTEM COMPRISING STAND AND MEDICAMENT DELIVERY DEVICE

CROSS REFERENCE TO RELATED APPLICATIONS

The present claims priority to European Patent Application No. 18207446.8 filed on Nov. 21, 2018 which is incorporated by reference into the present application.

TECHNICAL FIELD

The present disclosure generally relates to a stand for an elongated medicament delivery device. In particular, a stand for holding an elongated medicament delivery device in a vertical orientation, and a system comprising an elongated medicament delivery device and a stand, are provided.

BACKGROUND

Some types of medicaments can be stored for a long time and may be filled in containers, such as cartridges, syringes, ampoules, canisters or the like, containing a ready-to-use medicament in liquid state. However, some types of medicaments are a mixture of two substances, typically a medicament agent (such as lyophilized, powdered or concentrated liquid) and a diluent (such as water, dextrose solution or saline solution). These types of medicaments cannot be pre-mixed and stored for a long time because the medicament agent is unstable and will lose its effect quickly due to degradation. Hence, a user has to perform the mixing within a limited time period prior to the delivery of a dose of medicament by manually operating a medicament delivery device. If the mixing is not sufficient, the dose may comprise both gas and medicament. In this case, the dose of medicament may be smaller than intended.

In order to facilitate the mixing, a number of containers for mixing have been developed comprising at least two chambers, known as multi-chamber containers. Multi-chamber containers typically comprise a first chamber containing the medicament agent and at least one second chamber containing the diluent. These chambers may be sealed off with a stopper such that the medicament agents do not become degraded. When the medicament agent is to be mixed shortly before administering, redirecting passages are opened between the chambers. The passages allow the mixing of the medicament agent and the diluent.

During mixing, the medicament delivery device should typically be oriented substantially vertically in order to allow gases to escape. After sufficient mixing, typically several minutes, the medicament is ready for delivery. Some users find it inconvenient to hold the medicament delivery device in a vertical orientation by hand during mixing, in particular elder or disabled users.

SUMMARY

One object of the present disclosure is to provide a stand for an elongated medicament delivery device, which stand improves user experience.

A further object of the present disclosure is to provide a stand for a medicament delivery device, which stand enables elongated medicament delivery devices of different forms and/or sizes to be held in a substantially vertical orientation on a substantially horizontal support surface.

A still further object of the present disclosure is to provide a stand for a medicament delivery device, which stand has a simple and/or cheap design.

A still further object of the present disclosure is to provide a stand for a medicament delivery device, which stand is simple to manufacture.

A still further object of the present disclosure is to provide a stand for a medicament delivery device, which stand is strong.

A still further object of the present disclosure is to provide a stand for a medicament delivery device, which stand solves several or all of the foregoing objects in combination.

A still further object of the present disclosure is to provide a system comprising an elongated medicament delivery device and a stand for supporting the medicament delivery device, which system solves one, several or all of the foregoing objects.

A still further object of the present disclosure is to provide a method of supporting an elongated medicament delivery device, which method solves one, several or all of the foregoing objects.

According to one aspect, there is provided a stand for an elongated medicament delivery device having a distal end and a proximal end, the stand comprising a base section for supporting the stand on a support surface; a holding section for receiving the distal end of the medicament delivery device; and a body section arranged between the base section and the holding section; wherein the holding section is configured to hold the medicament delivery device in a substantially vertical orientation when the base section is positioned on the support surface. The holding section comprises an elastically deformable material for providing an elastic squeeze fit around the distal end of the medicament delivery device when received in the holding section. The support surface may for example be horizontal, or substantially horizontal.

The elastic squeeze fit is a tight fit of the holding section around the distal end. The holding section may comprise, or be constituted by, an elastically deformable material, such as an elastic material. That is, the holding section may partly or entirely be composed of the elastically deformable material. The holding section may fully enclose a central axis of the stand. The holding section may or may not be rotationally symmetric about the central axis of the stand. Throughout the present disclosure, an elastically deformable material may be configured to stretch at least 3%, such as at least 5%, before break.

The elastically deformable material enables a distal end with a larger outer circumferential length, than an inner circumferential length of the holding section in a neutral state of the holding section, to be held by the holding section. In other words, the holding section can be expanded to firmly hold the distal end of the medicament delivery device. This is advantageous since an elongated medicament delivery device may have a rather high center of gravity. In addition, this allows elongated medicament delivery devices with different forms and/or sizes to be firmly held by the holding section. The stand is therefore at least partly generic, and not only suitable for only one specific type of medicament delivery device.

The holding section may form a receptacle for the distal end. The receptacle may have a depth along the central axis of at least 50%, such as at least 70%, of a height of the stand along the central axis.

The stand may be configured to hold an elongated medicament delivery device such that a longitudinal axis of the medicament delivery device is coaxial, or substantially coaxial, with the central axis of the stand. The stand may be rotationally symmetric about the central axis of the stand.

The body section may be constituted by a hood. The body section may be directly or indirectly connected to, or joined with, the holding section. The body section may be rotationally symmetric about the central axis of the stand. The body section may be convex and/or hollow.

Throughout the present disclosure, the stand may alternatively be referred to as a support device, foot or cap. The stand constitutes an accessory for elongated medicament delivery devices. The stand may be used multiple times with different medicament delivery devices.

The stand may be used to hold the medicament delivery device in a substantially vertical orientation during priming (e.g. mixing of a diluent and a medicament contained in a medicament delivery device). The stand may also be used to hold the medicament delivery device when opening a cap of the medicament delivery device. The stand may further be used for stable storage of a medicament delivery device, for example on an instrument panel in a car.

The stand may be integrally formed of an elastically deformable material. For example, the stand may be injection molded, such as entirely injection molded. Each of the base section, the holding section and the body section may be formed of an elastically deformable material.

The stand may be made of one of rubber, soft plastic, PVC (polyvinyl chloride) and silicone. The rubber may be synthetic rubber.

The base section may provide a substantially flat base surface, or flat base surface, for supporting the stand on the support surface. The base surface may comprise a friction increasing structure and/or may be provided with a high-friction material. The high-friction material may be of the same or similar type as used in non-slip dashboard pads for mobile phones. Alternatively, or in addition, the base surface may be sticky, e.g. by means of glue. The base section may comprise silicone.

The stand may comprise a chamber configured to be sealingly closed by the support surface, and the stand may be configured such that an underpressure can be established in the chamber by pressing the medicament delivery device, while being held by the holding section, towards the base section enabling the stand to be sucked to the support surface. When the holding section moves towards the base section by pressing the medicament delivery device, air is pushed out from the chamber to create the underpressure. The stand is then sucked onto the support surface. This works for arbitrarily oriented support surfaces, but the support surface has to be smooth to provide the suction effect.

When the medicament delivery device is held vertically by the stand sucked onto a horizontal support surface, the medicament delivery device can be removed from the stand by pulling the medicament delivery device upwards with only one hand, i.e. without holding the stand with the other hand.

The base section may comprise a base opening. In this case, the base section may form a seal around the base opening for sealingly closing the base opening against a smooth support surface.

The holding section may comprise a holding section receiving opening having one of a circular, oval and polygonal shape for holding the medicament delivery device distal end of the corresponding shape. For example, the holding section and the base section may be circular.

The body section may be flexible. The flexibility of the body section facilitates the establishment of an underpressure in the chamber.

The stand may be configured to adopt a tubular state in which each of the holding section, the body section and the base section is configured to enclose the medicament delivery device. In this case, the stand may be manufactured in the tubular state.

The stand may be configured to be inverted from the tubular state to an inverted state by folding the body section relative to the holding section such that the holding section passes through a base opening of the base section; and the stand may in the inverted state be configured to hold the medicament delivery device in the substantially vertical orientation when the base section is positioned on the support surface. The stand may then be said to constitute a flip stand.

In the tubular state, the stand may be compactly arranged around the medicament delivery device. This is for example useful when packing a toiletry bag. After inverting the stand to the inverted state by folding the body section, the body section may be folded back such that the stand again adopts the tubular state.

The base section may comprise, or be constituted by, an elastically deformable material. Thereby, the base section is made expansible such that the holding section can pass through the base section when the base section adopts an expanded state.

The stand may comprise a hinge or a weakened region between the holding section and the body section that defines a fold line, e.g. an annular fold line substantially concentric with the central axis of the stand. Furthermore, in this variant, the body section may be flexible or stretchable. This also facilitates the folding of the body section.

The stand may be configured to hold the distal end of the medicament delivery device both in the tubular state and while the body section is folded.

The base section may be constituted by an end section of the body section. Alternatively, the base section may be directly or indirectly connected to, or joined with, the body section. The base section may be rotationally symmetric about the central axis of the stand. The base section may for example be constituted by a rim or flange. According to one variant, the base section comprises a circular flange that protrudes radially with respect to a center axis of the stand.

When the stand is produced in the tubular state, for example if the stand is integrally formed of an elastically deformable material, the inverting of the stand from the tubular state to the inverted state creates tensions in the material. These tensions increase the holding strength and structural strength of the stand.

A stand according to the present disclosure does however not necessarily need to be invertible. In this case, the stand may be said to constitute a ready-made stand. In the ready-made stand, at least the holding section may comprise an elastically deformable material. The body section and the base section of the ready-made stand may or may not be made of elastically deformable material. The body section and the base section of the ready-made stand may for example be rigid, or substantially rigid.

The base section may comprise at least one protrusion that protrudes radially with respect to a center axis of the stand. The at least one protrusion may protrude radially outwards when the stand adopts the tubular state. Conversely, the at least one protrusion may protrude radially inwards when the stand adopts the inverted state. When the stand adopts the tubular state and the distal end of the medicament delivery device is held by the holding section, the at least one protrusion functions as anti-roll tabs preventing the medicament delivery device from rolling away. In addition, the at least one protrusion functions as a finger grip for being grasped by the user in order to fold the body section relative to the holding section.

The base section may for example comprise two protrusion or four protrusions. In any case, the protrusions may be substantially evenly distributed, or evenly distributed, around the central axis of the stand.

According to a further aspect, there is provided a system comprising an elongated medicament delivery device and a stand according to the present disclosure for supporting the medicament delivery device. Throughout the present disclosure, the medicament delivery device may be an injection device for injecting a medicament, such as a drug mixture, by a user.

According to a further aspect, there is provided a method of supporting an elongated medicament delivery device having a distal end and a proximal end, the method comprising providing a stand comprising a base section for supporting the stand on a support surface, a holding section for receiving the distal end of the medicament delivery device, and a body section comprising an elastically deformable material arranged between the base section and the holding section; inserting the distal end into the holding section such that the holding section holds the distal end with an elastic squeeze fit; folding the body section relative to the holding section such that the holding section passes through a base opening of the base section and such that the stand adopts an inverted state while the distal end of the medicament delivery device is held by the holding section; placing the base section on a substantially horizontal support surface such that the medicament delivery device is held in a substantially vertical orientation, or vertical orientation, by the stand.

BRIEF DESCRIPTION OF THE FIGURES

Further details, advantages and aspects of the present disclosure will become apparent from the following embodiments taken in conjunction with the drawings, wherein.

DETAILED DESCRIPTION

Figure 1:
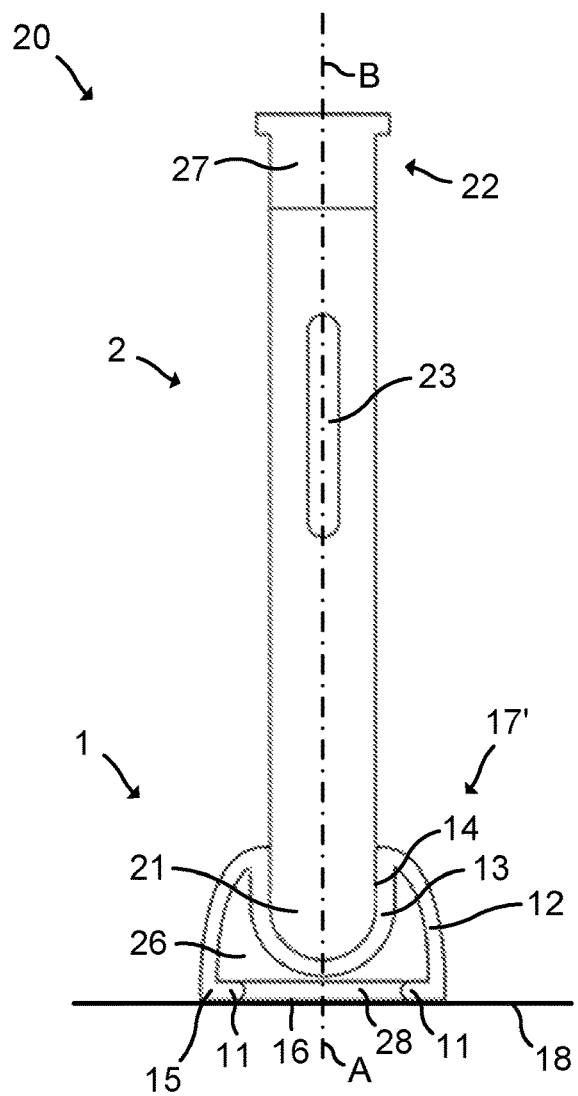
FIG. 1 schematically represents a side view of a system comprising a stand and a medicament delivery device held by the stand.

In the following, a stand for holding an elongated medicament delivery device in a vertical orientation, and a system comprising an elongated medicament delivery device and a stand, will be described. The same reference numerals will be used to denote the same or similar structural features.

FIG. 1 schematically represents a side view of a system 20 comprising a stand 1 and an elongated medicament delivery device 2 held by the stand 1. The stand 1 is illustrated in a cross-sectional view.

In this example, the medicament delivery device 2 is an injection device. However, the system 20 may comprise an alternative elongated medicament delivery device 2.

The stand 1 supports the medicament delivery device 2 on a horizontal support surface 18. In this example, the support surface 18 is also smooth.

The stand 1 has a central axis A. The medicament delivery device 2 has a longitudinal axis B. The medicament delivery device 2 comprises a distal end 21 and a proximal end 22. The medicament delivery device 2 of this example further comprises a cap 27 and an indicator window 23.

When the stand 1 is placed on the support surface 18 as in FIG. 1, the central axis A is vertical. When the stand 1 holds the medicament delivery device 2 as in FIG. 1, the longitudinal axis B is also vertical. As shown in FIG. 1, the central axis A and the longitudinal axis B are coaxial.

The stand 1 comprises a base section 15. The base section 15 provides a support for the stand 1 on the support surface 18. In this example, the base section 15 provides a flat base surface 16. The base section 15 comprises a base opening 28. In this example, the base opening 28 is enclosed by the base surface 16. The base surface 16 forms a seal around the base opening 28.

The stand 1 further comprises a holding section 13. The holding section 13 holds the distal end 21 of the medicament delivery device 2. The holding section 13 comprises an elastically deformable material. In this example, the holding section 13 is constituted by an elastically deformable material. That is, the entire holding section 13 is formed of an elastically deformable material. The elastically deformable material of this example has a stretchability of at least 5%.

The stand 1 further comprises a body section 12. The body section 12 is arranged between the base section 15 and the holding section 13. In this example, the body section 12 forms a bridge from the base section 15 to the holding section 13. The body section 12 adjoins both the base section 15 and the holding section 13.

As shown in FIG. 1, the holding section 13 is configured to hold the medicament delivery device 2 in the vertical orientation when the base section 15 is positioned on the support surface 18. The elastically deformable material provides an elastic squeeze fit around the distal end 21 of the medicament delivery device 2. The holding section 13 is slightly expanded to provide a tight fit around the distal end 21.

In the example in FIG. 1, the distal end 21 of the medicament delivery device 2 has a circular outer circumference. The holding section 13 comprises a holding section receiving opening 14. In the example in FIG. 1, the holding section receiving opening 14 is also circular. The inner diameter of the holding section receiving opening 14 is slightly smaller than the outer diameter of the distal end 21 in a neutral state of the holding section 13, i.e. when the medicament delivery device 2 is removed from the stand 1.

Due to the elastically deformable material, the holding section 13 having a circular holding section receiving opening 14 may hold distal ends 21 of different shapes and/or sizes. The holding section receiving opening 14 may however alternatively be oval or polygonal, such as triangular, to hold a distal end 21 with a substantially corresponding profile and size. The holding section receiving opening 14 is however still made smaller than the distal end 21 (in the neutral state of the holding section 13), such that the squeeze fit on the distal end 21 can be achieved.

The stand 1 in FIG. 1 comprises a chamber 26. The stand 1 of this example is thus hollow. The chamber 26 is configured to be sealingly closed by the support surface 18, which in this example is smooth. An underpressure can be established in the chamber 26 by pressing the medicament delivery device 2 towards the base section 15 (downwards in FIG. 1) while the distal end 21 of the medicament delivery device 2 is held by the holding section 13. During the pressing, some air escapes from the chamber 26 under the base surface 16 and the volume of air in the chamber 26 is reduced. In this way, the stand 1 can be firmly held against the support surface 18 by a suction force dictated by the underpressure in the chamber 26.

In this example, the chamber 26 is formed by the holding section 13, the body section 12 and the base section 15. As shown in FIG. 1, the chamber 26 is closed by the support surface 18.

The base section 15 of this example comprises two protrusions 11. Each protrusion 11 protrudes radially with respect to the center axis A. As shown in FIG. 1, each protrusion 11 protrudes radially inwards with respect to the center axis A. The protrusions 11 form part of the base surface 16.

Figure 2:
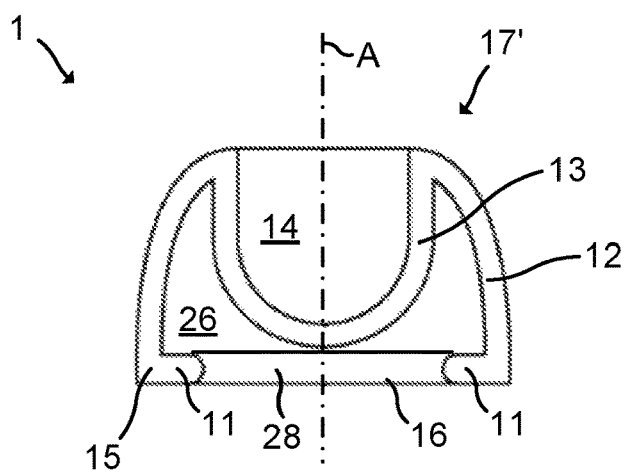
FIG. 2 schematically represents a side view of the stand in FIG. 1.

FIG. 2 schematically represents an enlarged cross-sectional side view of the stand 1 in FIG. 1. The stand 1 in FIGS. 1 and 2 is integrally formed of an elastically deformable material, such as rubber. Thus, the entire stand 1 is elastic and flexible. The flexibility of the body section 12 facilitates the establishment of the underpressure in the chamber 26. The stand 1 may for example be injection molded.

Furthermore, the stand 1 of the example in FIGS. 1 and 2 is rotationally symmetric about the central axis A. Each of the body section 12 and the base section 15 is circular. However, the stand 1 does not necessarily have to be symmetric or circular. As can be gathered from FIG. 2, the receptacle formed by the holding section 13 has a depth along the central axis A that is approximately 70% of the height of the stand 1 along the central axis A.

The downwardly facing base surface 16 of the example in FIGS. 1 and 2 comprises a layer of silicone (not denoted). This silicone layer provides a high friction relative to the support surface 18. Thus, the base surface 16 both provides a seal for sealingly closing the chamber 26 against the support surface 18 and provides high frictional resistance against movements of the stand 1 relative to the support surface 18.

The stand 1 in FIGS. 1 and 2 is ready-made and thus has a pre-fabricated form 17'. That is, the stand 1 does not necessarily have to be capable of being folded between a tubular state and an inverted state.

Figure 3:
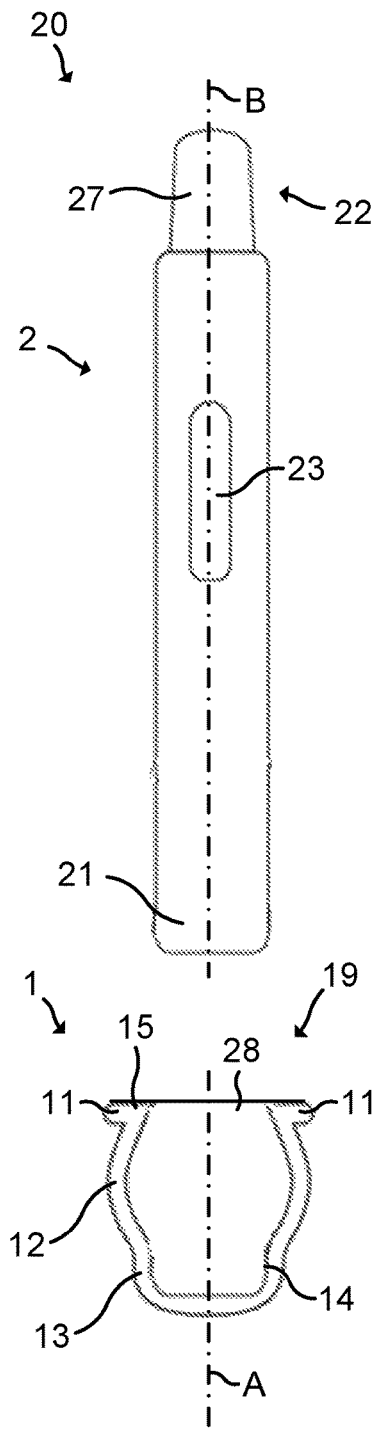
FIG. 3 schematically represents a side view of an alternative system comprising an alternative stand and a medicament delivery device before insertion of the medicament delivery device into the stand.

FIG. 3 schematically represents a side view of an alternative system 20 comprising an alternative stand 1 and a medicament delivery device 2 before insertion of the medicament delivery device 2 into the stand 1. Mainly differences with respect to FIGS. 1 and 2 will be described.

The medicament delivery device 2 in FIG. 3 differs from the medicament delivery device 2 in FIG. 1 by comprising a different type of cap 27 and a distal end 21 with a flat bottom (in contrast to the hemispherical bottom in FIG. 1). The medicament delivery device 2 of the example in FIG. 3 is an inhaler.

In FIG. 3, the stand 1 is in a tubular state 19. In the tubular state 19 of the stand 1, the holding section 13, the body section 12 and the base section 15 are sequentially arranged, i.e. one after the other, along the central axis A of the stand 1. In other words, the stand 1 generally forms a tube in the tubular state 19.

Figure 4:
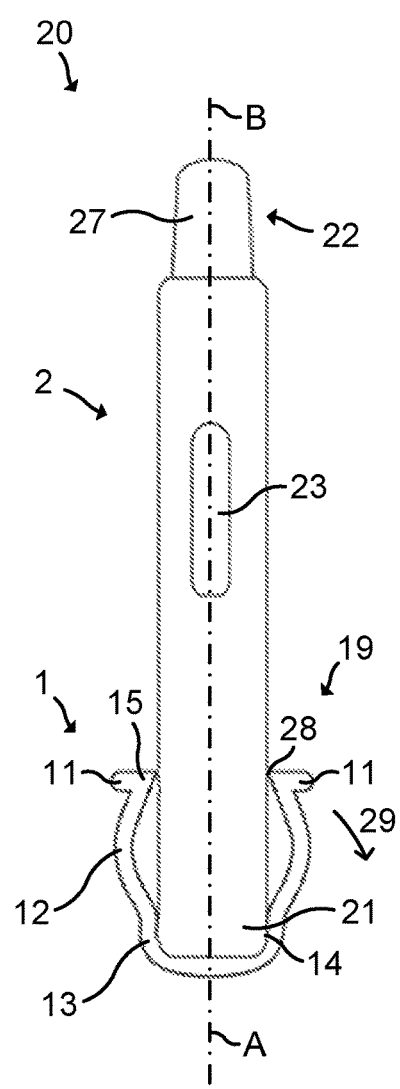
FIG. 4 schematically represents a side view of the system in FIG. 3 when the medicament delivery device has been inserted into the stand.

FIG. 4 schematically represents a side view of the system 20 in FIG. 3 when the medicament delivery device 2 has been inserted into the stand 1. In FIG. 4, each of the holding section 13, the body section 12 and the base section 15 encloses the distal end 21 of the medicament delivery device 2.

FIG. 4 further shows that the receptacle formed by the holding section 13 is of a slightly different shape than in FIG. 1. Both holding sections 13 comprise a circular holding section receiving opening 14. However, the bottom of the holding section 13 in FIG. 4 is flat while the bottom of the holding section 13 in FIG. 1 is hemispherical.

In the tubular state 19 in FIG. 4, the stand 1 is compactly arranged around the distal end 21. The body section 12 protrudes slightly radially outwards from the central axis A. Since also the base section 15 of this example comprises an elastically deformable material, also the base section 15 provides an elastic squeeze fit around the distal end 21.

As shown in FIG. 4, the protrusions 11 protrude radially outwards with respect to the central axis A and the longitudinal axis B. The protrusions 11 thereby serve as anti-roll tabs preventing the system 20 from rolling if laid horizontal on the support surface 18.

Figure 5:
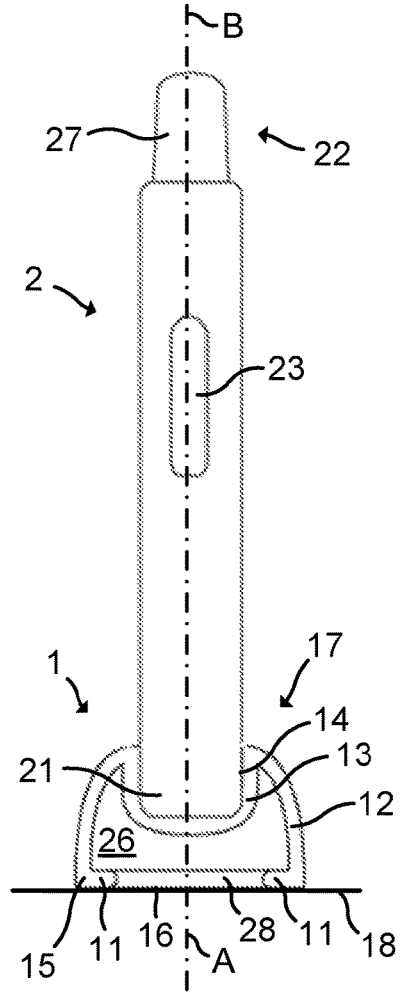
FIG. 5 schematically represents a side view of the system in FIGS. 3 and 4 when the stand has adopted an inverted state.

A user may grasp the protrusions 11 with his/her fingers and pull the base section 15 outwards and downwards, as indicated by arrow 29. This causes the body section 12 to fold relative to the holding section 13. The stand 1 can thereby be inverted from the tubular state 19 in FIG. 4 to an inverted state 17 as shown in FIG. 5. A weakened region may be provided between the holding section 13 and the body section 12 to define a fold line. During the inverting, the base section 15 expands such that the base opening 28 is made larger. In this expanded state of the base section 15, the base section 15 together with the body section 12 are folded downwards such that the holding section 13 eventually passes through the base opening 28.

FIG. 5 schematically represents a side view of the system 20 in FIGS. 3 and 4 when the stand 1 has adopted the inverted state 17. As shown in FIG. 5, the stand 1 holding the medicament delivery device 2 is positioned on the support surface 18. In the inverted state 17, the stand 1 in FIG. 5 has the same functions as the stand 1 in FIGS. 1 and 2. The holding section 13 holds the distal end 21 of the medicament delivery device 2 with an elastic squeeze fit such that the medicament delivery device 2 is vertically oriented. The chamber 26 is formed by the stand 1 when adopting the inverted state 17.

Furthermore, the stand 1 in FIG. 5 can be sucked onto the support surface 18 by pressing the medicament delivery device 2 towards the base section 15 (downwards in FIG. 5) such that an underpressure is established in the chamber 26. When the stand 1 is sucked onto the support surface 18, the medicament delivery device 2 can be removed from the stand 1 by lifting the medicament delivery device 2 upwards with one hand, without holding the stand 1 with the other hand.

If desired, the stand 1 may be folded back again from the inverted state 17 in FIG. 5 to the tubular state 19 in FIG. 4. This may be done while the distal end 21 is held by the holding section 13.

The stand 1 may be produced in the tubular state 19, such that the elastically deformable material of the stand 1 is in a non-tensioned or relaxed condition, or low-tension condition, in the tubular state 19. When the stand 1 is deformed into the inverted state 17, tensions in the stand 1 makes the stand 1 stronger.

Figure 6:
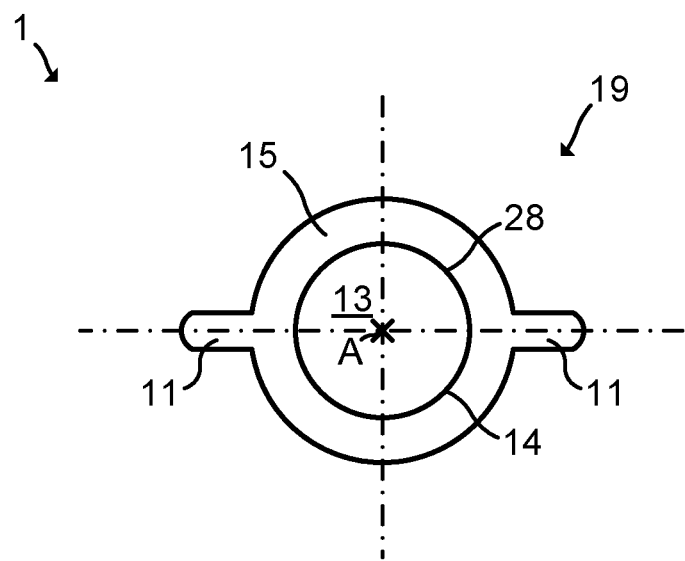
FIG. 6 schematically represents a top view of the stand in FIGS. 3-5 in a tubular state.

FIG. 6 schematically represents a top view of the stand 1 in FIGS. 3-5 in the tubular state 19. FIG. 6 shows that the two protrusions 11 are oppositely arranged on the base section 15.

Figure 7:
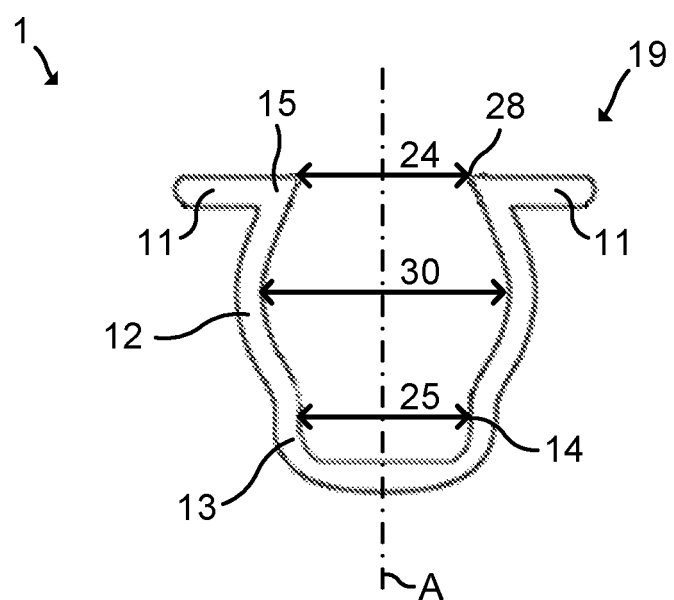
FIG. 7 schematically represents a side view of the stand in FIG. 6.

FIG. 7 schematically represents a side view of the stand 1 in FIG. 6. As shown in FIG. 7, in the neutral unbiased state of the stand 1, an inner diameter 24 of the base section 15 equals an inner diameter 25 of the holding section 13. An inner diameter 30 of the body section 12 is slightly larger than the inner diameters 24, 25.

While the present disclosure has been described with reference to exemplary embodiments, it will be appreciated that the present invention is not limited to what has been described above. For example, it will be appreciated that the dimensions of the parts may be varied as needed.

The invention claimed is:

1. A stand for an elongated medicament delivery device having a distal end and a proximal end, the stand comprising:
   a center axis;
   a tubular state and an inverted state;
   a base section comprising a protrusion for supporting the stand on a support surface when the stand is in the inverted state such that the protrusion projects radially inwards with respect to the center axis;
   a holding section comprising a receiving opening terminating in a bottom surface configured for receiving and supporting the distal end of the medicament delivery device when the stand is in both the inverted and tubular state, where the bottom surface is positioned below the base section when the stand is in the tubular state and where the bottom surface is positioned above the base section when the stand is in the inverted state; and
   a body section arranged between the base section and the holding section;
   wherein the holding section is configured to hold the medicament delivery device in a substantially vertical orientation when the base section is positioned on the support surface; and
   wherein the holding section comprises an elastically deformable material for providing an elastic squeeze fit around the distal end of the medicament delivery device when received in the holding section.

2. The stand of claim 1, further comprising a fold line between the body section and the holding section.

3. The stand of claim 1, wherein when the stand is in tubular state, the protrusion projects radially outward relative to the center axis.

4. The stand of claim 1, wherein a chamber is formed between the bottom surface and the base section when the stand changes from the tubular state to the inverted state.

5. The stand of claim 2, wherein the base section further comprises at least two protrusions that are configured to be grasped by a user when the stand is in the tubular state and pulled outward and downward relative to the center axis such that the body section folds along the fold line relative to the holding section to transform the stand into the inverted state.

6. The stand according to claim 1, wherein the stand is integrally formed of an elastically deformable material.

7. The stand according to claim 1, wherein the stand is made of one of rubber, soft plastic, PVC and silicone.

8. The stand according to claim 1, wherein the base section provides a substantially flat base surface for supporting the stand on the support surface.

9. The stand according to claim 8, wherein the base surface comprises a friction increasing structure or is provided with a high-friction material.

10. The stand according to claim 1, wherein the stand comprises a chamber configured to be sealingly closed by the support surface when the stand is in the inverted state, and wherein the stand is configured such that an under pressure can be established in the chamber by pressing the medicament delivery device, while being held by the holding section, towards the base section enabling the stand to be sucked to the support surface.

11. The stand according to claim 1, wherein the receiving opening having one of a circular, oval and polygonal shape for holding the medicament delivery device distal end of the corresponding shape.

12. The stand according to claim 1, wherein the body section is flexible.

13. The stand according to claim 1, wherein the stand is configured to transform from the inverted to the tubular state in which each of the holding section, the body section and the base section is configured to enclose the medicament delivery device.

14. The stand according to claim 1, wherein the base section comprises a circular flange that protrudes radially with respect to the center axis of the stand.

15. A system comprising an elongated medicament delivery device and a stand according to claim 1 for supporting the medicament delivery device.

* * * * *